(12) United States Patent
Kuo et al.

(10) Patent No.: US 8,390,805 B2
(45) Date of Patent: Mar. 5, 2013

(54) SURFACE ENHANCED RAMAN SPECTROSCOPY SYSTEM

(75) Inventors: Huei Pei Kuo, Cupertino, CA (US); Zhiyong Li, Redwood City, CA (US); R. Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 348 days.

(21) Appl. No.: 12/846,524

(22) Filed: Jul. 29, 2010

(65) Prior Publication Data

US 2012/0154791 A1     Jun. 21, 2012

(51) Int. Cl.
    *G01J 3/44*        (2006.01)
(52) U.S. Cl. ....................................... 356/301
(58) Field of Classification Search .................... 356/301
    See application file for complete search history.

(56) References Cited

U.S. PATENT DOCUMENTS

| | | | |
|---|---|---|---|
| 5,982,497 A * | 11/1999 | Hopkins | 356/419 |
| 7,267,948 B2 | 9/2007 | Vo-Dinh | |
| 7,355,710 B2 * | 4/2008 | Gfrorer et al. | 356/417 |
| 7,391,511 B1 * | 6/2008 | Bratkovski et al. | 356/301 |
| 7,560,285 B2 * | 7/2009 | Sun | 436/164 |
| 7,656,523 B2 * | 2/2010 | Sun et al. | 356/301 |
| 2006/0001868 A1 * | 1/2006 | Stewart et al. | 356/301 |
| 2008/0219926 A1 | 9/2008 | Vo-Dinh | |
| 2009/0109271 A1 | 4/2009 | Studer et al. | |
| 2010/0079753 A1 | 4/2010 | Hehlen | |
| 2012/0113420 A1 * | 5/2012 | Kuo et al. | 356/301 |

FOREIGN PATENT DOCUMENTS

WO    WO 2009/123630    10/2009

* cited by examiner

*Primary Examiner* — Gregory J Toatley
*Assistant Examiner* — Shawn Decenzo (57) ABSTRACT

A surface enhanced Raman spectroscopy system includes a surface enhanced Raman spectroscopy substrate and a laser source configured to emit light within a spectrum of wavelengths toward a predetermined species on or near the surface enhanced Raman spectroscopy substrate. The system further includes a set of filters positioned to be in optical communication with light scattered after the laser light interacts with the predetermined species. Each of the filters in the set is respectively configured to pass scattered light within a different predetermined narrow band of wavelengths. The system also includes a plurality of photodetectors, where each photodetector is positioned adjacent to a respective one of the filters in the set and is configured to output a signal if the scattered light passes through the respective one of the filters. The set of filters is targeted for detection of characteristic peaks of the predetermined species.

18 Claims, 6 Drawing Sheets

SURFACE ENHANCED RAMAN SPECTROSCOPY SYSTEM

BACKGROUND

The present disclosure relates generally to surface-enhanced Raman spectroscopy systems.

Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species. As such, Raman spectroscopy is a useful technique for a variety of chemical or biological sensing applications. However, the intrinsic Raman scattering process is very inefficient, and rough metal surfaces, various types of nano-antennas, as well as waveguiding structures have been used to enhance the Raman scattering processes (i.e., the excitation and/or radiation process described above). This field is generally known as surface enhanced Raman spectroscopy (SERS).

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Embodiments of the surface enhanced Raman spectroscopy system disclosed herein is configured with predefined filter sets with narrow wavebands for analysis of characteristic or fingerprint peaks of a particular species. Some embodiments of the system are configured for parallel analysis of the characteristic peaks of one species, while other embodiments of the system are configured for parallel analysis of the characteristic peaks of a number of different species. The filter set can be fixed within the system, or removable from the system. Removable filter sets make the system modular, and provide the advantage that different species can be analyzed simply by inserting a different filter set. The peaks analyzed will depend upon the design of the filter set that is put into an active position in the system. As used herein, the term "active position" means that the filter set is aligned with photodetectors of the system and can receive light scattered from a surface enhanced Raman spectroscopy substrate having the predetermined species on or near its surface.

Figure 1:
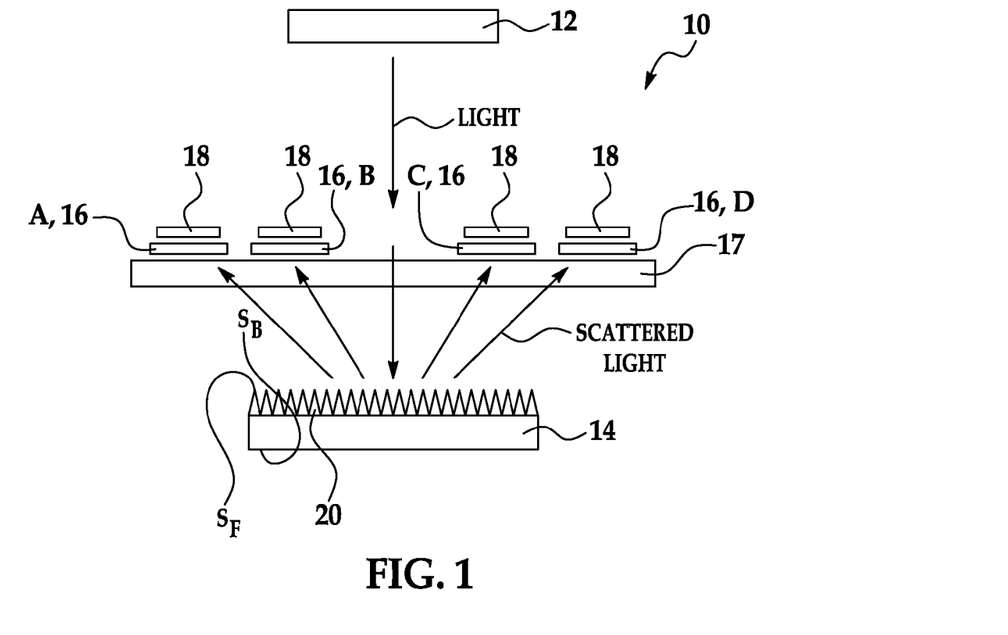
FIG. 1 is a schematic view of an embodiment of a surface enhanced Raman spectroscopy system.

Referring now to FIG. 1, an embodiment of the system 10 is depicted. The system 10 generally includes a laser source 12, a surface enhanced Raman spectroscopy (SERS) substrate 14, a filter set 16 including a plurality of filters A, B, C, D, and a plurality of photodetectors 18.

The laser source 12 has a narrow spectral line width and is selected to emit light within the visible range or within the near-infrared range. The laser source 12 may be selected from a steady state laser or a pulsed laser. The laser source 12 is positioned to project light onto the surface enhanced Raman spectroscopy substrate 14. A lens (not shown) and/or other optical equipment (e.g., optical microscope) may be used to direct (e.g., bend) the laser light in a desired manner. In one embodiment, the laser source 12 is integrated on a chip. The laser source 12 is also operatively connected to a power supply.

The SERS substrate 14 is a substrate having nano-features 20 (e.g., antennas (see FIG. 5), pillars, poles, flexible columnar or finger-like structures (see FIG. 4), cone-shaped structures (see FIG. 1), multi-faceted nanostructures, etc.) formed thereon. Examples of suitable SERS substrates and/or methods for making these substrates are described in the following International or U.S. Patent Application Serial Numbers: PCT/US09/57327, filed Sep. 17, 2009 and entitled "Electrically Driven Devices for Surface Enhanced Raman Spectroscopy"; PCT/US10/31790, filed Apr. 20, 2010 and entitled "Multi-Pillar Structure for Molecular Analysis"; PCT/US10/31809, filed Apr. 20, 2010 and entitled "A Self-Arranging, Luminescence Enhancement Device for Surface-Enhanced Luminescence"; PCT/US09/49911, filed Jul. 8, 2009 and entitled "Light Amplifying Devices for Surface Enhanced Raman Spectroscopy"; and 12/771,440, filed Apr. 30, 2010 and entitled "Surface-enhanced Raman Spectroscopy Device and a Mold for Creating and a Method for Making the Same"; all of which are incorporated herein by reference.

Generally, the nano-features 20 may be any metal or metal-coated plasmonic nano-structures (i.e., having at least one dimension ranging from about 1 nm to about 100 nm) that amplify the Raman scattering from a molecule (i.e., analyte, species of interest, predetermined species) when exposed to laser illumination. The metal or metal-coating is a Raman signal enhancing material, or a material that is capable of increasing the number of Raman scattered photons when the molecule (or other species of interest) is located proximate to the nano-feature 20, and when the molecule and material are subjected to electromagnetic radiation. Raman signal-enhancing materials include, but are not limited to, silver, gold, and copper.

The portion of the substrate 14 upon which the nano-features 20 are formed may be transparent or reflective depending upon the position of the substrate 14 in the system 10. If the filter set 16 is positioned across from the front surface $S_F$ (i.e., the surface being illuminated by the laser source 12) of the substrate 14, the substrate 14 may be selected from reflective and/or non-reflective materials. Non-limiting examples of suitable substrates include germanium, silicon, or transparent substrates such as, e.g., glass, quartz, nitrides, alumina, sapphire, transparent polymers (e.g., polycarbonate, polyimide, acrylic, etc.), combinations thereof, and/or layers thereof. In an example, the transparent substrate includes a reflective mirror on a back surface $S_B$ of the substrate 14. However, if the filter set 16 is positioned across from the back surface $S_B$ (i.e., the surface opposed to the illuminated surface $S_F$), the substrate 14 is selected from transparent materials so that scattered light may be transmitted through the substrate 14 to the filter set 16. The latter embodiment is discussed further in reference to FIG. 4. Non-limiting examples of suitable transparent substrates include glass, quartz, nitrides, alumina, sapphire, transparent polymers (e.g., polycarbonate, polyimide, acrylic, etc.), or combinations or layers thereof.

It is to be understood that since Raman scattering is isotropic, Raman photons may be collected in a reflective mode or in a transmission mode depending upon the transparency of the substrate 14. In some instances, the collection efficiency may be increased by placing an antenna on a reflective mirror substrate.

The set of filters 16 includes multiple filters A, B, C, D. Each of the filters A, B, C, D is designed or selected to allow a peak or dominant transmission in a specific region or narrow waveband. The "narrow waveband" refers to all of the wavelengths within the small bandwidth of the filter A, B, C, D, where the small bandwidth ranges from about 0.06 nm to about 10 nm, or from about 2 nm to about 8 nm, or from about 1 nm to about 5 nm. In one embodiment, the narrow wavebands of the respective filters A, B, C, D do not overlap. In other embodiments, the narrow wavebands of the respective filters A, B, C, D, may partially overlap. Similarly, the wavelengths within the narrow wavebands of the respective filters A, B, C, D may or may not be continuous from one filter to the next.

In one embodiment, filters A, B, C, D having the desirable narrow wavebands include those used in optical communications. Examples of other suitable filters A, B, C, D include, but are not limited to stacked layers of dielectric materials, dielectric gratings (e.g., a subwavelength dielectric grating filter), interference filters (e.g., Fabry Perot filters), or any other filter having a narrow waveband.

The filters A, B, C, D, in one particular set 16 are selected to correspond with the characteristic wavelength peaks of a predetermined species. For the following example, the filters selected are for the Stokes Raman shift, and the illumination laser is a 633 nm laser. In this example, the species of interest (i.e., predetermined species) is cocaine hydrochloride having characteristic Raman peaks of 786 $cm^{-1}$ (approximately 666 nm), 851 $cm^{-1}$ (approximately 669 nm), 870 $cm^{-1}$ (approximately 670 nm), 894 $cm^{-1}$ (approximately 671 nm), 999 $cm^{-1}$ (approximately 676 nm)), 1596 $cm^{-1}$ (approximately 704 nm), and 1709 $cm^{-1}$ (approximately 710 nm). The set 16 may include seven corresponding filters A, B, C, D, etc., such as one for detecting wavelengths of 666±1 nm, one for detecting wavelengths of 669±1 nm, one for detecting wavelengths of 670±0.5 nm, one for detecting wavelengths of 671±0.5 nm, one for detecting wavelengths of 676±1 nm, one for detecting wavelengths of 704±1 nm, and one for detecting wavelengths of 710±2 nm. It is to be understood that this is one non-limiting example, and that the filter set 16 may be designed to include any number of filters A, B, C, D for filtering the characteristic peaks of a desired species.

Figure 2A:
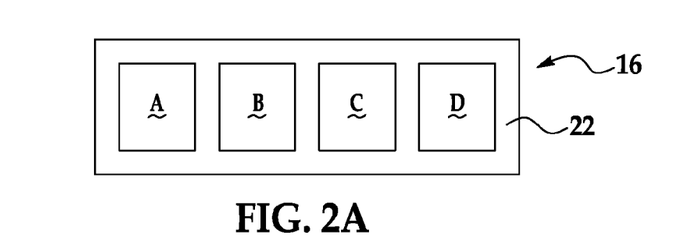
FIGS. 2A through 2C are schematic top views of embodiments of filter sets suitable for use in embodiments of the surface enhanced Raman spectroscopy system.
Figure 2B:
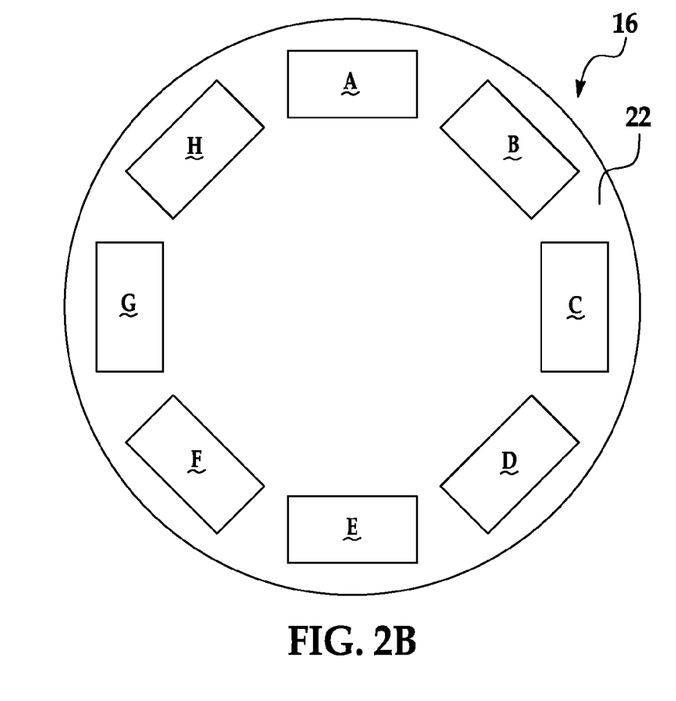

In one embodiment, each of the filters A, B, C, D of the set 16 is integrated into/onto a single support 22. Non-limiting examples are shown in FIGS. 2A and 2B. In one embodiment, the support 22 is glass. The support 22 may have any suitable shape, including, for example, a strip (FIG. 2A) or a wheel (FIG. 2B). In another embodiment, the filters A, B, C, D, E, F, G, H are prefabricated filters that are adhered to (e.g., glued on (e.g., using an epoxy)) or otherwise bonded to the support 22. An example of these prefabricated filters includes dielectric filters. In another embodiment, the filters A, B, C, D, E, F, G, H are patterned in the support 22 in any desirable pattern that corresponds with the pattern of the photodetectors 18 in the system 10. Patterning of the filters A-H may be accomplished using photolithography. More particularly, photolithography may be used to define the gratings for a particular frequency response directly on the substrate 22. In either embodiment, the filters A, B, C, D, E, F, G, H are positioned so that when the filter set 16 is permanently or temporarily in an active position in the system 10, each filter A, B, C, D, E, F, G, H aligns with a respective photodetector 18. When adhesives are used, it is to be understood that the glue or other adhesive used is selected so as to not interfere with the transmission of the desired wavelengths through the respective filters A, B, C, D, E, F, G, H, etc.

Figure 2C:
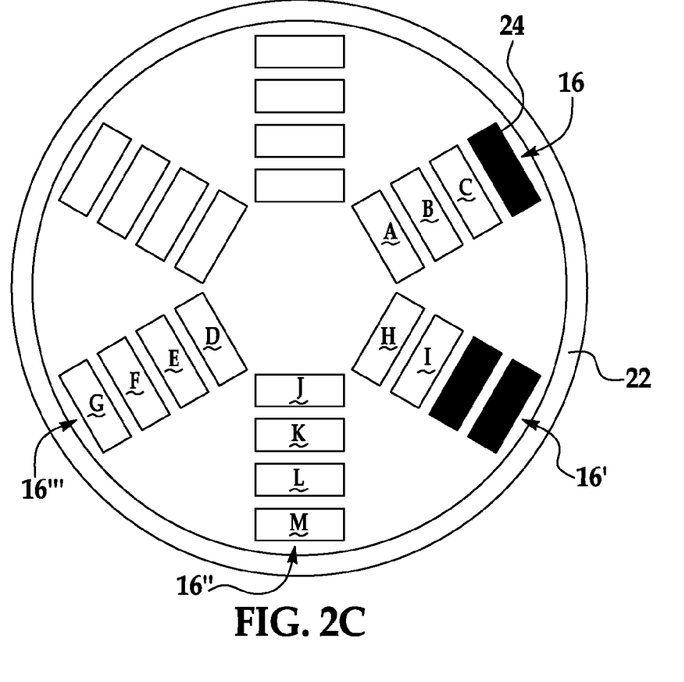

FIG. 2C illustrates another embodiment in which multiple filter sets 16, 16', 16", 16"', etc. are integrated into/onto a single support 22. In this embodiment, each filter set 16, 16', 16", 16"' may be designed for a different species. For example, the filters A, B, C of set 16 may be selected to filter the characteristic peaks of alcohol, while the filters D, E, F and G of set 16"' may be selected to filter the characteristic peaks of E-coli, the filters H and I of set 16' may be selected to filter the characteristic peaks of the explosive C4, and the filters J, K, L and M of set 16" may be selected to filter the characteristic peaks of marijuana. While the remaining two filter sets shown in FIG. 2C are not labeled, it is to be understood that the filters of these sets may also be selected to filter the characteristic peaks of some other desired substances.

The embodiment shown in FIG. 2C may be used for sequential analysis of the various species, or for parallel analysis of the various species. For sequential analysis, the system 10 used may include four photodetectors 18 positioned to align with any one of the filter sets 16, 16', 16", 16"' at any given time. As such, the support 22 may be dialed in to a particular filter set 16, 16', 16", 16"' such that the filters of one set, for example filters A, B, and C of set 16, are aligned with the four photodetectors 18 of the system 10. When the filter set 16, 16', 16", 16"' that is to be dialed in includes fewer filters (e.g., A, B, C or H, I) than the number of photodetectors 18 in the system 10, a light blocking layer 24 may be included where a filter would otherwise be positioned. This layer 24 will reduce or eliminate the transmittance of incident light or scattered light to the photodetector 18 adjacent to the light blocking layer 24. For parallel analysis, the system 10 used may include photodetectors 18 that will align with each of the filters in the respective filter sets 16, 16', 16", 16"' at the same time. As such, each of the filter sets 16, 16', 16", 16"' is in an active position simultaneously. This may be particularly desirable when testing a blood sample because multiple species (e.g., alcohol, various drugs, etc.) may be analyzed simultaneously.

Referring back to FIG. 1, the filter set 16 (and support 22, not shown in FIG. 1) may be fixed within the system 10, or may be selectively removable from the system 10. When fixed, the support 22 is mounted so that each filter A, B, C, D of the set 16 is permanently aligned with a corresponding photodetector 18. When removable, the filter set 16 can be inserted into the system 10 and removed from the system 10. When a removable filter set 16 is inserted, the support 22 is temporarily mounted so that each filter A, B, C, D is or can be (e.g., when dialed in to the active position) aligned with a corresponding photodetector 18. The system 10 configured to be used with removable filter sets 16 can receive a plurality of filter sets 16 that are designed to fit into the system 10. This may be particularly desirable because, as previously described, different filter sets 16 can be designed for filtering characteristic peaks of different species, and thus a single system 10 can be used for detecting a variety of different species.

The embodiment of the system 10 shown in FIG. 1 also includes one photodetector 18 for each filter A, B, C, D, in the filter set 16. As such, in this embodiment, one photodetector 18 corresponds with and is positioned adjacent to one filter A, B, C, or D such that each photodetector 18 is positioned to receive any scattered light that passes through its corresponding filter A, B, C, or D. In embodiments in which multiple filter sets 16, 16', 16", 16''' are included on the same support 22 (see FIG. 2C), the system 10 may include one photodetector 18 for each filter of each set 16, 16', 16", 16''', or may include a preset number of photodetectors 18 that can be aligned with any one of the filter sets 16, 16', 16", 16''' at any given time. The magnitude of the output of the photodetector 18 is proportional to the amount of scattered light that reaches the photodetector 18, and thus is proportional to the amount of light passing through the corresponding filter A, B, C, or D. Each photodetector 18 may be selected from a photodiode, a phototransistor, an avalanche photodiode, a calibrator, or any other suitable photodetector.

In some embodiments, the system 10 may also include collection optics 17 (as shown in FIG. 1) positioned between the SERS substrate 14 and the filter set 16. Collection optics 17 can be selected from any suitable component (e.g., a lens, one or more mirrors, etc.) that collects the scattered light and directs (or re-directs/bends) the scattered light toward the filters A, B, C, D.

Figure 3:
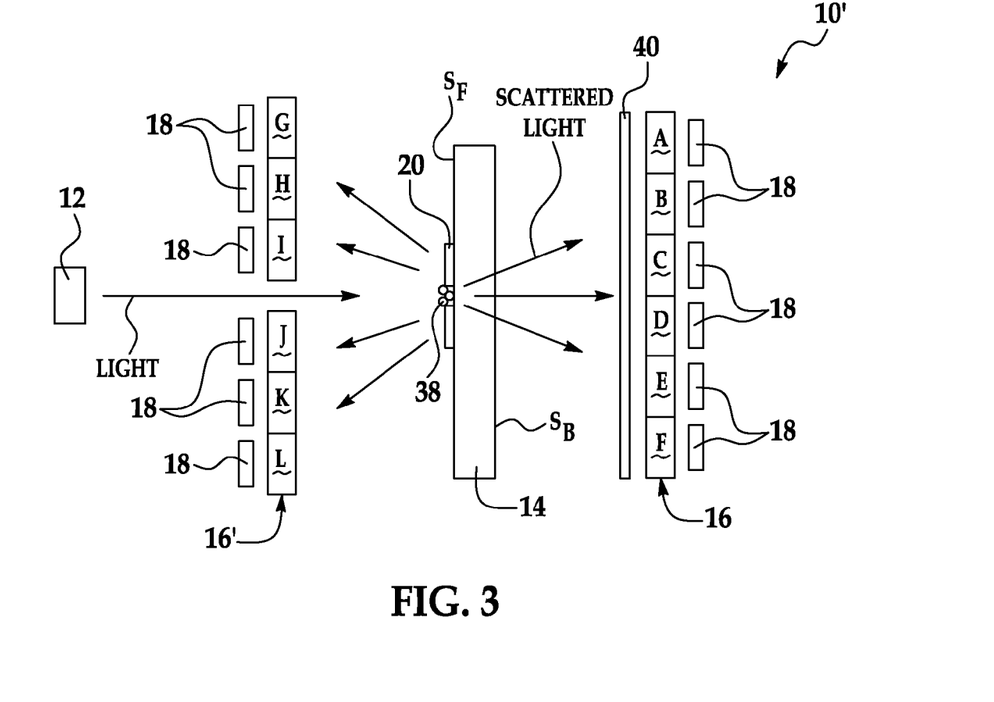
FIG. 3 is a schematic view of another embodiment of the surface enhanced Raman spectroscopy system.

FIG. 3 illustrates another embodiment of the system 10', which includes one filter set 16 or 16' and corresponding photodetectors 18 positioned across from each surface $S_F$, $S_B$ of the SERS substrate 14. In this embodiment, the substrate 14 is formed of a transparent material so that at least some of the scattered light (resulting from the interaction between the laser source light and the species 38) can be transmitted through to the filter set 16 across from the back surface $S_B$ of the SERS substrate 14.

FIG. 3 illustrates a gap formed in the filter set 16'. A similar gap is shown in the embodiment of FIG. 1. This gap is created to illustrate the allowance of the light from the laser source 12 to pass through to the SERS substrate 14. The gap is not drawn to scale, since the laser can be illuminated to the sample at a small offset angle from the filter set.

The embodiment of the system shown in FIG. 3 also includes another filter 40 positioned between the substrate 14 and the filter set 16. While one additional filter 40 is shown, it is to be understood that an additional filter 40 may be positioned between the substrate 14 and any filter sets 16, 16', etc. used in the system 10. This additional filter(s) 40 is not an analyzing filter with narrow wavebands (such as filters A-L), but rather is an incident light filter used to remove Rayleigh scattering photons that may otherwise overwhelm the narrow waveband filters A-L. Non-limiting examples of additional filter(s) 40 include bandpass filters or notch filters. Whether integrated into a system 10 that is configured with a fixed filter set or for receiving removable filter sets, the incident light filter 40 may be permanently fixed between the substrate 14 and either the fixed filter set or a mounting system configured to receive the removable filter sets.

Figure 4:
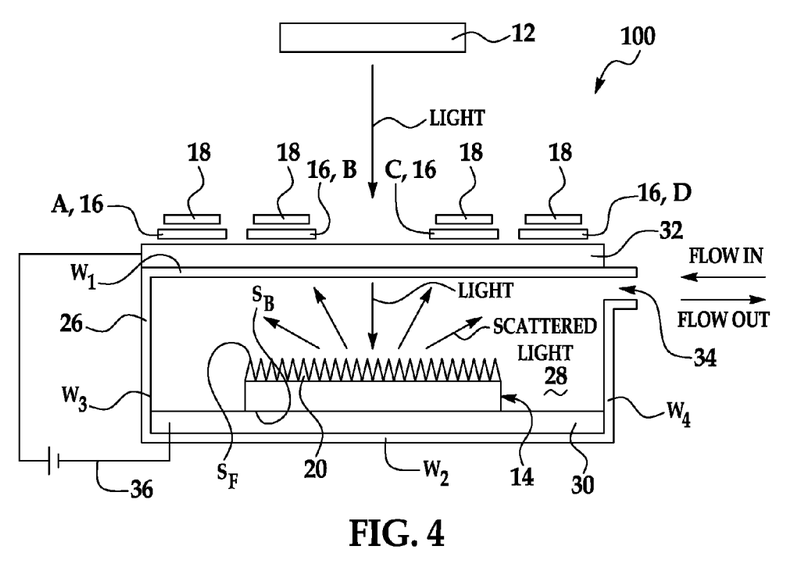
FIG. 4 is a schematic view of an embodiment of a flow-through system including an embodiment of the surface enhanced Raman spectroscopy system.
Figure 5:
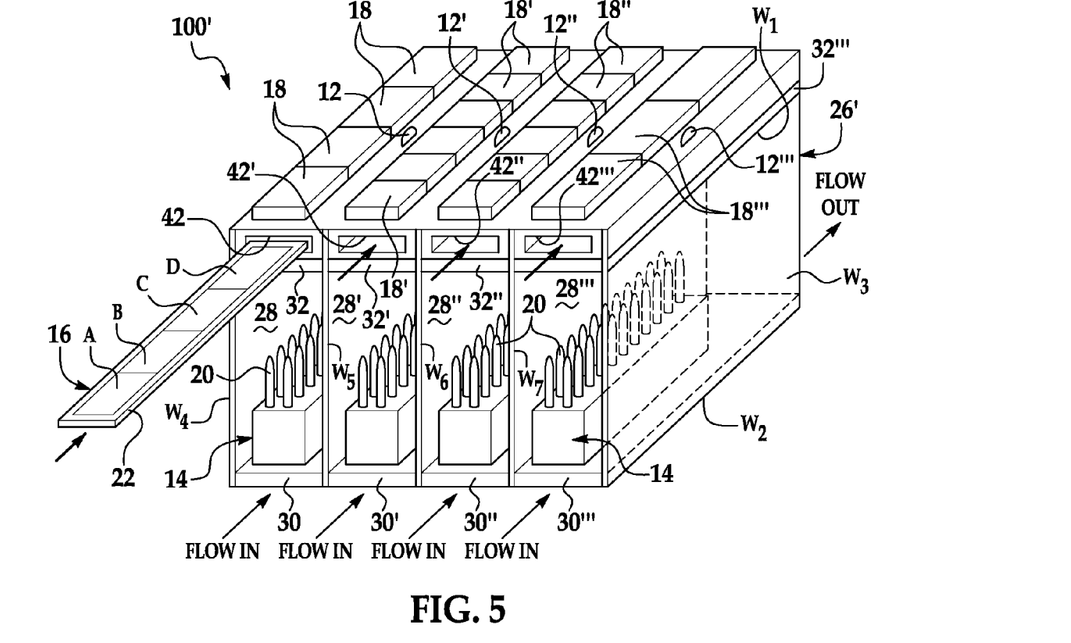
FIG. 5 is a semi-schematic perspective view of another embodiment of the flow-through system including an embodiment of the surface enhanced Raman spectroscopy system.
Figure 6:
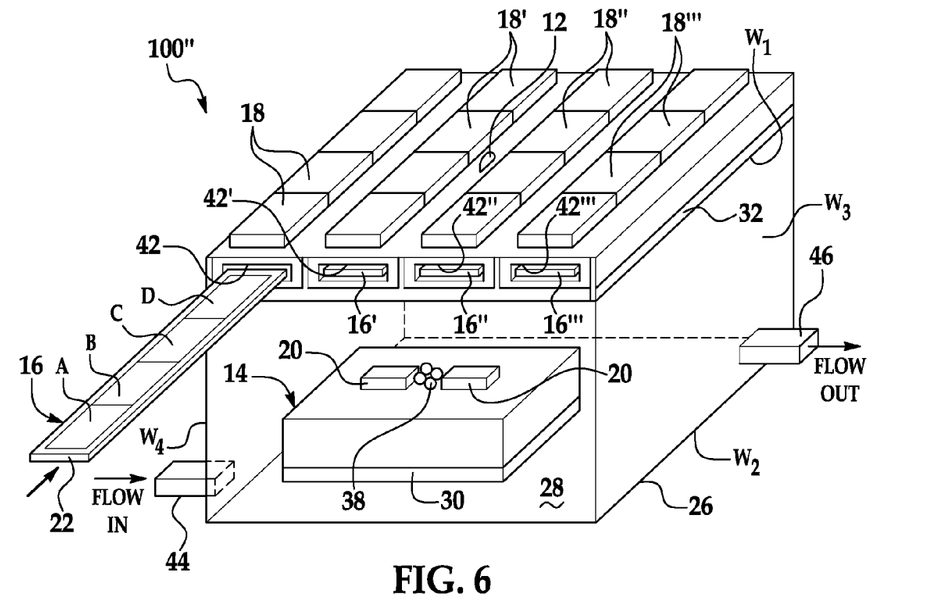
FIG. 6 is a semi-schematic perspective view of yet another embodiment of the flow-through system including an embodiment of the surface enhanced Raman spectroscopy system.
Figure 7A:
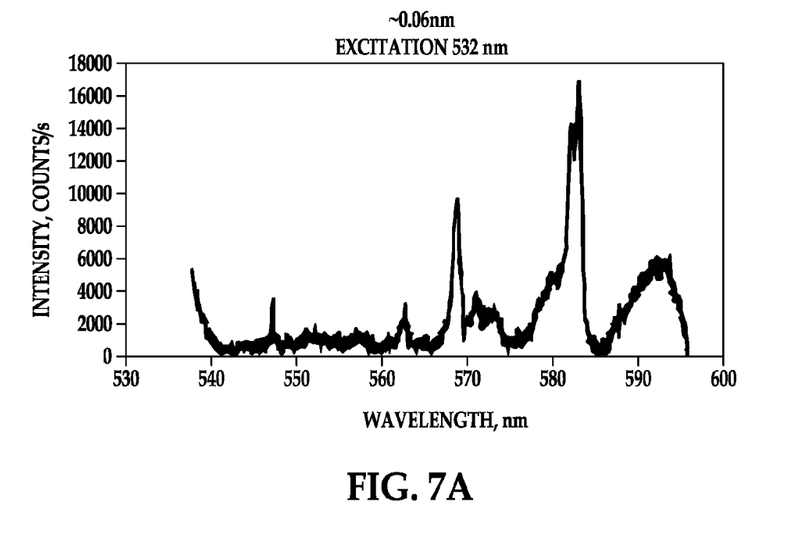
FIGS. 7A through 7E are Raman spectra for bispyridylethylene (BPE) molecules, each spectrum illustrating the appearance of the resolution as a function of pass bandwidth of the filter used.
Figure 7B:
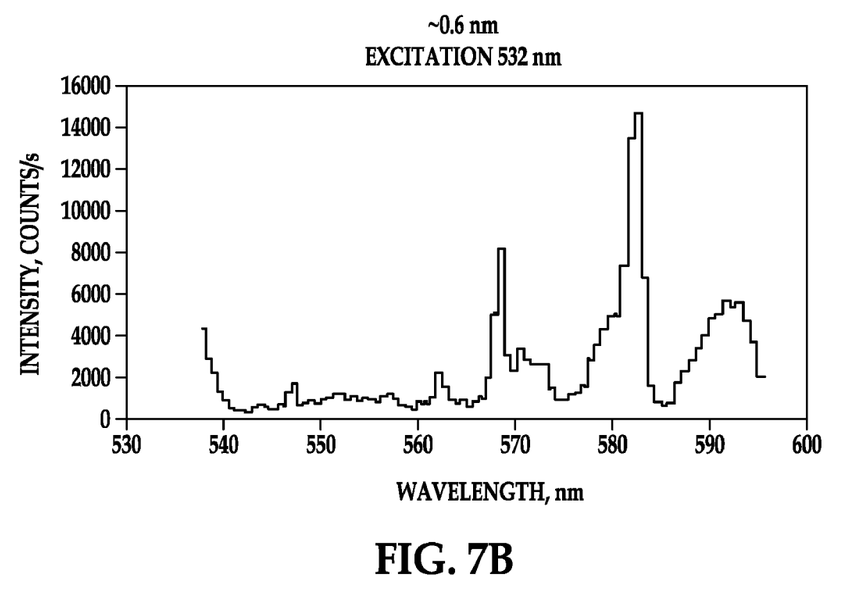
Figure 7C:
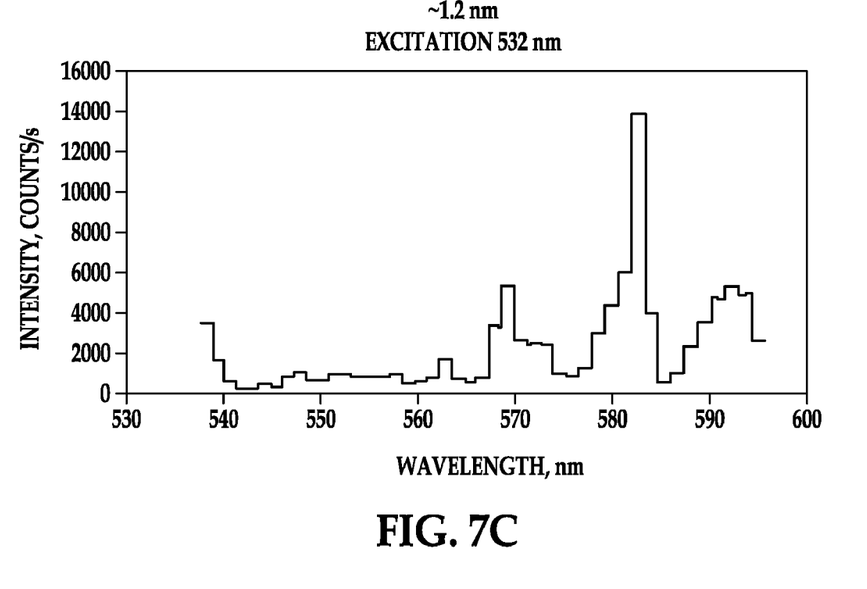
Figure 7D:
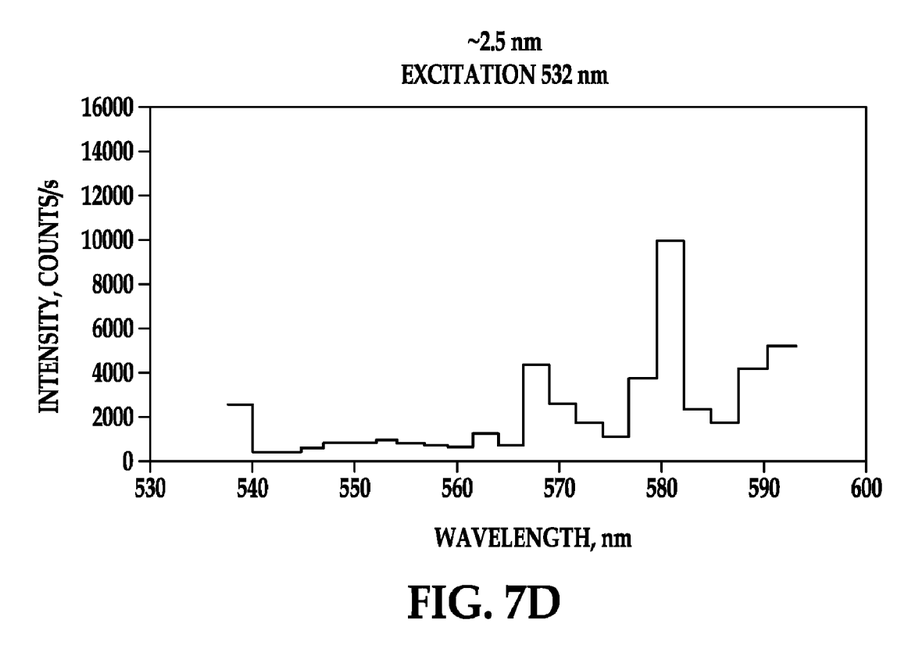
Figure 7E:
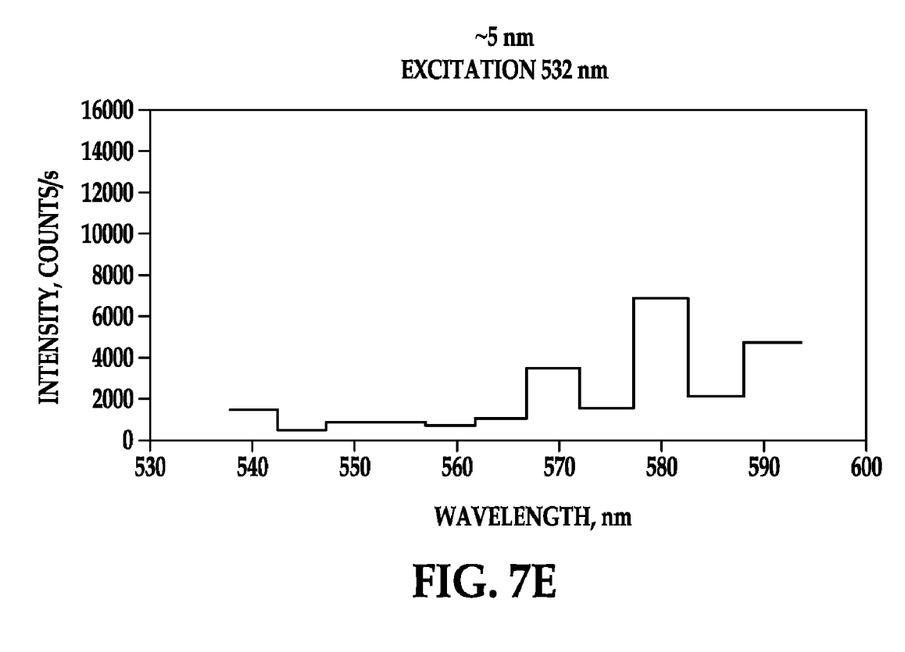

Referring now to FIG. 4, some embodiments of the system 10, 10' are included as part of a flow-through system 100 (other examples of which are shown in FIGS. 5 and 6). Flow-through systems 100 include the components of the system 10 or 10', and further include a chamber 26 that is configured to contain the SERS substrate 14 and have the predetermined species introduced thereto. The chamber 26 shown in FIG. 4 is a single channel cell including an enclosed interior portion 28 which defines the single channel. The enclosed interior portion 28 itself is defined by at least one surface/wall $W_1$ that is transparent to light (that will be used for Raman spectroscopy) and another surface/wall $W_2$ opposed to the at least one transparent surface $W_1$. In this embodiment, sides walls $W_3$, $W_4$ (and those front and back walls not shown) are attached to or formed integrally with each of the surfaces $W_1$, $W_2$ to enclose the portion 28. It is to be understood that since light is generally not introduced through the wall $W_2$ or the side walls $W_3$, $W_4$, such components may be formed of transparent, semi-transparent, or opaque materials. In particular, any material may be used to form $W_2$, and the side walls $W_3$, $W_4$, as long as the selected materials do not deleteriously affect the introduction of light into the chamber 26 or the transmission of scattered light (SERS signals) from the chamber 26 through the transparent wall $W_1$. In one embodiment, the regions of the wall $W_1$ that face the laser source 12 are optically smooth (e.g., there is no emission or scattering center on these surfaces and light can pass therethrough without significantly scattering (i.e., $d<\lambda/(8 \cos \theta)$, where d is the surface roughness (e.g., root-mean-square roughness height measured from a reference plane), $\lambda$ is the wavelength of the incident illumination, and $\theta$ is the angle of incidence of this illumination). As a non-limiting example, the wall $W_1$ is formed of quartz or transmissive plastics (e.g., acrylics), and the other walls $W_2$, $W_3$, $W_4$ are formed of quartz, glass, plastics, or steel.

The dimensions of the enclosed interior portion 28 will depend, at least in part, upon the desirable dimensions of the substrate 14 that will be positioned therein. As such, the walls $W_1$, $W_2$ are spaced apart sufficiently to accommodate the SERS substrate 14. As a non-limiting example, the total thickness of the chamber 26 is the desirable distance between electrodes 30, 32 used to enhance the electric field at or near the nano-features 20 of the substrate 14. In one example, the total thickness of the chamber 26 is about 0.5 mm. In another example, the total thickness of the chamber 26 is up to about 5 mm.

The electrode 32 is at least partially transparent to the light to be used for Raman spectroscopy, and the other electrode 30 (positioned proximate to the substrate 14) may or may not be transparent. The electrodes 30, 32 are positioned such that when an appropriate voltage bias is applied between the electrodes 30, 32, the electric field is enhanced at a desired portion of the nano-features (e.g., at the gap between nano-antennas or other nano-structures, at the tip of a nano-cone, etc.). Since SERS applications involve light of a suitable wavelength being directed toward the substrate 14, it is desirable that the electrode 32, which is positioned such that it faces the nano-features 20 of the substrate 14, is at least partially transparent to the light. Non-limiting examples of suitable transparent electrodes include indium tin oxide electrodes, Al- and Ga-doped ZnO (AZO and GZO), carbon, or the like. The other electrode 30 may be transparent or opaque as long as light is not to be transmitted therethrough. Examples of other electrode materials include metals, such as gold, platinum, aluminum, silver, tungsten, copper, etc. The electrodes 30, 32 shown in FIG. 4 have rectangular cross-sections, but it is to be understood that electrodes 30, 32 may also have circular, elliptical, or more complex cross-sections. The electrodes 30, 32 may also have many different widths or diameters and aspect ratios or eccentricities. Other examples of suitable electrodes 30, 32 include hollow electrodes, plate electrodes, or partially transparent electrodes that include conductive portions and optically transparent portions (e.g., formed of any material that is transparent to the desirable excitation wavelengths and the resulting SERS signals).

The electrodes 30, 32 may be acquired in a usable state or may be fabricated using conventional techniques, such as photolithography or electron beam lithography, or by more advanced techniques, such as, e.g., imprint lithography. It is to be understood that the electrodes 30, 32 may be any suitable size (ranging from a micrometer up to inches), and will depend, at least in part, upon the desirable SERS application for which it is being configured. In one embodiment, the size of each of the electrodes 30, 32 is comparable to the size of the SERS substrate 14. It is to be understood that since the electrode 30 in this embodiment is not used for light transmission, it may be thicker than the electrode 32.

As shown in FIG. 4, one of the electrodes 30 is positioned within the enclosed interior portion 28, and the other electrode 32 is positioned outside the enclosed interior portion 28. Both electrodes 30, 32 may be positioned outside of the enclosed interior portion 28. Similarly, both electrodes 32, 32 may be included within the enclosed interior portion 28. The latter configuration may be more desirable because the electrodes 30, 32 are physically closer to the SERS substrate 14. In such instances, however, it may be desirable to establish a protective coating (not shown) over the electrodes 30, 32 in order to reduce the potential for corrosion and/or adsorption of ions to the electrodes 30, 32. Examples of such protective electrode coating materials include glass, acrylic, or the like. When used to protect the electrode 32, it is to be understood that the material selected should be transparent to the excitation wavelengths and scatted light wavelengths (i.e., Raman signals). The protective coating is generally thin (i.e., less than 100 µm, and in some instances less than 5 nm).

The enclosed interior portion 28 includes at least one port 34 that is configured to introduce fluid (i.e., a liquid (e.g., water, ethanol, etc.) or gas (e.g., air, nitrogen, argon, etc.) containing or acting as a carrier for the analyte molecules) into the enclosed interior portion 28 and/or discharge the fluid from the enclosed interior portion 28. In the embodiment shown in FIG. 4, the port 34 is both a fluid inlet and a fluid outlet. Since the port 34 allows fluid ingress and egress, it may be fluidly coupled to a reservoir (not shown) which serves as both a sample injector and/or reaction chamber and a waste reservoir.

While not shown in FIG. 4, it is to be understood that in this embodiment, the substrate 14 is, in general, electrically connected to the bottom electrode 30 through a set of low electrical resistance contacts (e.g., a metal region on the top surface of substrate 14 or a metal bottom surface of the substrate 14 if substrate 14 is sufficiently conductive).

During operation of the flow through system 100 shown in FIG. 4, the enclosed interior portion 28 is filled with a solution (not shown) that contains some concentration of polarizable analyte molecules. The analyte molecules may settle on a surface of the SERS substrate 14 due to gravitational and/or chemical forces. Upon application of a voltage bias between the electrodes 30, 32 using a power source 36, the analyte molecules in solution are polarized and an electric field EF is generated. Application of the field EF during sample preparation increases the speed at which the analyte molecules settle on the substrate 14. The field strength generally increases at or near the nano-feature(s) 20, and the field gradient produces a net attractive force on the polarized molecules toward all or a portion of the nano-feature(s) 20. Thus, the molecules move attach or self-assemble in the proximities of the nano-features 20 where the electric field EF is most intense. It is to be understood that if the analyte molecules have a permanent charge, they will also experience a net force and be attracted to the nano-feature(s) 20. Generally, positively charged molecules require that the electrode 30 be biased negatively relative to the electrode 32, and negatively charged molecules require a reversed biasing.

After the sample containing the analyte molecules is prepared, the laser light is operated to emit light toward the substrate 14. The analyte molecules concentrated at or near the nano-features 20 of the substrate 14 interact with and scatter the electromagnetic radiation. The Raman scattered radiation is redirected toward the filters A, B, C, D, and the Raman scattered radiation having wavelengths within the respective wavebands of the filters A, B, C, D are allowed to pass through the respective filters A, B, C, D to an adjacent photodetector 18. The photodetectors 18 will emit a signal if light passes through its corresponding filter A, B, C, D. Furthermore, wavelengths that are not within the respective narrow waveband of the filters A, B, C, D are filtered out and do not pass through to the photodetectors 18.

FIG. 5 is a perspective view of another embodiment of a flow-through system 100'. This embodiment of the flow-through system 100' includes one chamber 26' having multiple fluidly separated interior portions 28, 28', 28'', 28''', and thus the chamber 26' is a multi-channel cell. A multi-channel cell is configured so that a single analysis can be performed using one of the interior portions 28, 28', 28'', 28''' and its associated components, or so that multiple analyses can be performed simultaneously using more than one interior portion 28, 28', 28'', 28''' and their respective associated components.

In this embodiment, the exterior walls of the chamber 26' include those walls previously described in conjunction with FIG. 3, namely $W_1$, $W_2$, $W_3$, and $W_4$, as well as the front and back walls (the front of which is not shown for clarity, and both of which are not labeled in FIG. 5). The chamber 26' also includes interior walls $W_5$, $W_6$, and $W_7$ which divide the chamber 26' into four separate interior portions 28, 28', 28'', 28'''. As previously mentioned, in this embodiment each interior portion 28, 28', 28'', 28''' may be used for analysis of a different species, and thus it is desirable that scattered light does not travel from one interior portion 28, 28', 28'', 28''' into any other interior portion 28, 28', 28'', 28''', but rather is directed toward a filter set and photodetectors associated with a particular interior portion 28, 28', 28'', 28'''. As such, interior walls $W_5$, $W_6$, and $W_7$ are made of opaque materials, such as steel.

This embodiment of the flow-through system 100' includes multiple insertion receptacles 42, 42', 42'', 42''', each of which is configured to removably receive a respective filter set (e.g., filter set 16 shown in FIG. 5). The receptacles 42, 42', 42'', 42''' are positioned so that when a respective filter set (e.g., filter set 16) is inserted therein, the filters of the filter set are aligned with corresponding photodetectors 18, 18', 18'', 18''' that are positioned above the insertion receptacles 42, 42', 42'', 42'''. As such, for the embodiment shown in FIG. 5, receptacle 42 can removably receive filter set 16 having four filters A, B, C, D, whereas receptacles 42', 42", and 42'" can removable receive filter sets (not shown) including seven, six, and three filters, respectively.

The receptacles 42, 42', 42", 42'" are also positioned so that when a respective filter set (e.g., set 16) is inserted, scattered light that contacts the filters (e.g., filters A, B, C, D) is transmitted from within an associated interior portion 28, 28', 28", 28'", and not from an adjacent interior portion 28, 28', 28", 28'". For example, light scattered from molecules on or near the SERS substrate 14 in interior portion 28 should be directed toward the inserted filter set 16 and its corresponding, aligned photodetectors 18.

As illustrated in FIG. 5, each of the interior portions 28, 28', 28", 28'" is able to house a respective SERS substrate 14 and includes respective fluid inlets and outlets for introduction and removal of different species. While the SERS substrates 14 shown in FIG. 5 are similar, it is to be understood that different SERS substrates 14 may be placed into each of the interior portions 28, 28', 28", 28'".

In the embodiment shown in FIG. 5, each of the interior portions 28, 28', 28", 28'" is also associated with its own electrodes 30 and 32, 30' and 32', 30" and 32", 30'" and 32'" (which have their own power sources, not shown) and laser sources 12, 12', 12", 12'". The respective electrode pairs and laser sources are independently addressable and operable from each of the other electrode pairs and laser sources. As such, the embodiment of the flow-through system 100' shown in FIG. 5 essentially includes four distinct analysis systems that can be operated separately from one another. Therefore, this embodiment of the flow-through system 100' may be used to perform a single analysis, or multiple analyses at the same time or at different times.

FIG. 6 is a perspective view of another embodiment of a flow-through system 100". This embodiment of the flow-through system 100" includes one chamber 26 having a separate fluid inlet 44 and outlet 46. The inlet 44 may be connected to one or more other devices, such as a sample injector and/or reaction chamber. The analyte molecules 38 may enter the interior portion 36 of the chamber 26 and pass across the Raman active substrate 14, where they may be exposed to stimulating/excitation wavelengths from the laser source 12, and the resulting signals may be detected by the photodetectors 18 (i.e., when the scatter light passes through a corresponding filter). Once analysis is complete, the sample including the analyte molecules 38 may be ejected through the outlet 46.

In this embodiment, the exterior walls of the chamber 26 include those walls previously described in conjunction with FIG. 1, namely $W_1$, $W_2$, $W_3$, and $W_4$, as well as the front and back walls (the front of which is not shown for clarity, and both of which are not labeled in FIG. 6).

This embodiment of the flow-through system 100" includes multiple insertion receptacles 42, 42', 42", 42'", each of which is configured to removably receive a respective filter set (e.g., filter sets 16, 16', 16", 16'"). The receptacles 42, 42', 42", 42'" are positioned so that when a respective filter set 16, 16', 16", 16'" is inserted therein, the filters of the filter set are aligned with corresponding photodetectors 18, 18', 18", 18'" that are positioned above the insertion receptacles 42, 42', 42", 42'".

In this embodiment, the scattered light is able to contact any of the filters (e.g., filters A, B, C, D) of the filter sets 16, 16', 16", 16'" that are inserted into the receptacles 42, 42', 42", 42'". For example, light scattered from molecules on or near the SERS substrate 14 is directed toward each of the inserted filter sets 16, 16', 16", 16'" and the corresponding, aligned photodetectors 18, 18', 18", 18'". Since the receptacles 42, 42', 42", 42'" can each contain a different filter set 16, 16', 16", 16'" (which can be configured to detect characteristic peaks of different analyte molecules), a single sample can be tested for multiple analyte molecules. As one example, the system 10'" could be used to test a blood or urine sample for alcohol and various drugs as long as one of the filter sets 16 is designed to pass the characteristic peak wavelengths of alcohol, while the other of the filter sets 16', 16", 16'" are each designed to pass the characteristic peak wavelengths of the various drugs.

This embodiment of the flow-through system 100" may also include the electrodes 30, 32 and laser source 12 previous described. It is to be understood that an electrical feedthrough (not shown) may be provided through one of the walls $W_3$ so that the power source 20 may be operatively connected to the substrate 14 and electrode 30 when the chamber 26 is in the closed and sealed position (e.g., when plugs are used to seal the inlet 44 and outlet 46. It is to be understood that the feedthrough may be formed in any of the walls $W_1$, $W_2$, $W_3$, $W_4$, front, or back, as long as the electrical connection made allows a voltage difference to be applied between the electrodes 30 and 32.

In any of the embodiments disclosed herein, photodetectors 18 (or 18', 18", 18'") may also be operably coupled to a computer (not shown) which can process, analyze, store and/or transmit data about the species being analyzed.

Furthermore, in any of the embodiments disclosed herein including fixed filter sets 16, 16', 16", 16'", the filters of the sets 16, 16', 16", 16'" and the photodetectors 18, 18', 18", 18'" may be predisposed on an integrated circuit.

Still further, in any of the embodiments disclosed herein, the light from the laser source 12 may be directed toward the substrate 14 at any desirable angle, and is not limited to being directed normal to the substantially flat surface of the substrate 14 having the nano-features 20 thereon.

To demonstrate the importance of using narrow bandwidth filters for the embodiments of the system 10, 10' disclosed herein, an example of the bispyridylethylene Raman spectrum acquired with different filter bandwidths is shown in FIGS. 7A through 7E. The bandwidths of the filters shown are 0.06 nm, 0.6 nm, 1.2 nm, 2.5 nm, and 5 nm, respectively. These results illustrate that the narrower the bandwidth of the filter that is used, the sharper the spectrum that can be obtained.

It is to be understood that the ranges provided herein include the stated range and any value or sub-range within the stated range. For example, an amount ranging from about 0.06 nm to about 10 nm should be interpreted to include not only the explicitly recited amount limits of about 0.06 nm to about 10 nm, but also to include individual amounts, such as 2 nm, 3 nm, 4 nm, etc., and sub-ranges, such as 5 nm to 10 nm, 3 nm to 6 nm, etc. Furthermore, when "about" is utilized to describe a value, this is meant to encompass minor variations (up to +/−10%) from the stated value.

While several embodiments have been described in detail, it will be apparent to those skilled in the art that the disclosed embodiments may be modified. Therefore, the foregoing description is to be considered non-limiting.

What is claimed is:

1. A surface enhanced Raman spectroscopy system, comprising:
   a chamber configured to have a predetermined species introduced thereto;
   a surface enhanced Raman spectroscopy substrate contained in the chamber, the surface enhanced Raman spectroscopy substrate having nano-features on a surface thereof;

first and second electrodes positioned to enhance an electric field at a predetermined portion of the nano-features when a voltage bias is applied between the first and second electrodes, the first electrode facing the nano-features and being transparent to light within a spectrum of wavelengths and the second electrode being proximate to a surface of the surface enhanced Raman spectroscopy substrate that is opposed to the surface having the nano-features thereon;

a laser source configured to emit light within the spectrum of wavelengths through a transparent wall of the chamber and toward the predetermined species on or near the surface enhanced Raman spectroscopy substrate;

a set of filters positioned adjacent to the transparent wall of the chamber to be in optical communication with light scattered after the laser light interacts with the predetermined species, each of the filters in the set being respectively configured to pass scattered light within a different predetermined narrow band of wavelengths; and a plurality of photodetectors, each photodetector being positioned adjacent to a respective one of the filters in the set and being configured to output a signal if the scattered light passes through the respective one of the filters;

wherein the set of filters is targeted for detection of characteristic peaks of the predetermined species.

2. The surface enhanced Raman spectroscopy system as defined in claim 1 wherein the set of filters is a removable set of filters.

3. The surface enhanced Raman spectroscopy system as defined in claim 2, further comprising a second removable set of filters which, when placed in an active position, is in optical communication with the laser source, each of the filters in the second set being respectively configured to pass scattered light within a second predetermined narrow band of wavelengths, wherein the second set of filters is targeted for detection of characteristic peaks of a second predetermined species that is different from the predetermined species.

4. The surface enhanced Raman spectroscopy system as defined in claim 3, further comprising multiple insertion receptacles, each of which is configured to removably receive a respective one of the first and second sets of filters for parallel analysis of the predetermined species and the second predetermined species.

5. The surface enhanced Raman spectroscopy system as defined in claim 3 wherein the filters of the set and the filters of the second set are each fabricated on a respective strip or a respective wheel that is selectively removable from the system.

6. The surface enhanced Raman spectroscopy system as defined in claim 1 wherein the chamber includes multiple fluidly separated interior portions, wherein the first set of filter is a removable set of filters, and wherein the system further comprises:

a second surface enhanced Raman spectroscopy substrate contained in one of the multiple fluidly separated interior portions which is physically isolated from an other of the multiple fluidly separated interior portions containing the surface enhanced Raman spectroscopy substrate, the second surface enhanced Raman spectroscopy substrate having second nano-features on a surface thereof;

a second set of first and second electrodes positioned to enhance an electric field at a predetermined portion of the second nano-features when a voltage bias is applied between the second set of first and second electrodes, the first electrode of the second set facing the second nano-features and being transparent to light within a second spectrum of wavelengths and the second electrode of the second set being proximate to a surface of the second surface enhanced Raman spectroscopy substrate that is opposed to the surface having the second nano-features thereon;

a second laser source configured to emit light within the second spectrum of wavelengths through the transparent wall of the chamber and toward a second predetermined species on or near the second surface enhanced Raman spectroscopy substrate;

a second set of filters positioned adjacent to the transparent wall of the chamber to be in optical communication with scattered light after the second laser light interacts with the second predetermined species, each of the filters in the second set being respectively configured to pass scattered light within a different predetermined narrow band of wavelengths;

a second plurality of photodetectors, each photodetector of the second plurality being positioned adjacent to a respective one of the filters in the second set and being configured to output a signal if the scattered light passes through the respective one of the filters in the second set; and an insertion receptacle associated with each of the multiple fluidly separated interior portions and positioned such that the first and second removable sets of filters can be in active positions simultaneously for parallel analysis of the predetermined species and the second predetermined species.

7. The surface enhanced Raman spectroscopy system as defined in claim 1 wherein the set of filters is a glass substrate having the filters pre-patterned thereon.

8. The surface enhanced Raman spectroscopy system as defined in claim 1 wherein each of the filters in the set has a bandwidth ranging from about 0.06 nm to about 5 nm.

9. The surface enhanced Raman spectroscopy system as defined in claim 8 wherein each of the filters in the set is an interference filter, a subwavelength dielectric grating filter, or a filter including multiple dielectric layers.

10. The surface enhanced Raman spectroscopy system as defined in claim 1 wherein the laser source is a visible range laser source or a near-infrared laser source.

11. The surface enhanced Raman spectroscopy system as defined in claim 1 wherein the nano-features are selected from at least two nanopoles, at least two flexible columnar structures, at least two cone-shaped nanostructures, and at least two multi-faceted nanostructures.

12. The surface enhanced Raman spectroscopy system as defined in claim 1 wherein the surface enhanced Raman spectroscopy substrate is configured to be exposed to a gas containing the predetermined species or a liquid containing the predetermined species.

13. The surface enhanced Raman spectroscopic system as defined in claim 1 wherein a configuration of the set of filters and the plurality of photodetectors enables parallel analysis of the characteristic peaks of the predetermined species.

14. The surface enhanced Raman spectroscopy device as defined in claim 1 wherein each of the plurality of photodetectors is a photo diode.

15. The surface enhanced Raman spectroscopy device as defined in claim 1, further comprising an incident light filter positioned between the set of filters and the surface enhanced Raman spectroscopy substrate.

16. The surface enhanced Raman spectroscopy device as defined in claim 1 wherein the first electrode is positioned outside of the chamber and wherein the second electrode is positioned inside of the chamber.

17. The surface enhanced Raman spectroscopy device as defined in claim 1 wherein the first electrode and the second electrode are positioned inside of the chamber.

18. The surface enhanced Raman spectroscopy device as defined in claim 1 wherein the first electrode and the second electrode are positioned outside of the chamber.

* * * * *

UNITED STATES PATENT AND TRADEMARK OFFICE
CERTIFICATE OF CORRECTION

PATENT NO. : 8,390,805 B2  
APPLICATION NO. : 12/846524  
DATED : March 5, 2013  
INVENTOR(S) : Huei Pei Kuo et al.

Page 1 of 1

It is certified that error appears in the above-identified patent and that said Letters Patent is hereby corrected as shown below:

In the Claims:

In column 12, line 55, in Claim 13, delete "spectroscopic" and insert -- spectroscopy --, therefor.

In column 12, line 59, in Claim 14, delete "device" and insert -- system --, therefor.

In column 12, line 62, in Claim 15, delete "device" and insert -- system --, therefor.

In column 12, line 66, in Claim 16, delete "device" and insert -- system --, therefor.

In column 13, line 3, in Claim 17, delete "device" and insert -- system --, therefor.

In column 14, line 1, in Claim 18, delete "device" and insert -- system --, therefor.

Signed and Sealed this  
First Day of October, 2013

Teresa Stanek Rea  
*Deputy Director of the United States Patent and Trademark Office*